United States Patent
Wecker et al.

(10) Patent No.: US 6,320,084 B2
(45) Date of Patent: Nov. 20, 2001

(54) PROCESS FOR THE PREPARATION OF GLYCERALDEHYDE AND DERIVATIVES THEREOF

(75) Inventors: Ulrich Wecker, Wuppertal; Manfred Josef Bergfeld, Erlenbach-Mechenhard, both of (DE)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/793,220

(22) Filed: Feb. 26, 2001

(30) Foreign Application Priority Data

Feb. 25, 2000 (EP) .................................................. 00200669

(51) Int. Cl.⁷ .......................... C07C 45/00; C07C 47/02; C07C 27/00; C07C 27/04; C07B 41/00
(52) U.S. Cl. ...................... 568/469; 568/469.9; 568/496; 568/497; 568/385; 568/861; 568/862; 564/397
(58) Field of Search .............................. 568/469, 469.9, 568/496, 497, 385, 861, 862; 564/397

(56) References Cited

U.S. PATENT DOCUMENTS

| | | | |
|---|---|---|---|
| 2,947,761 | 8/1960 | Payne ................ | 260/348.5 |
| 3,962,338 | 6/1976 | Weinstock et al. .......... | 260/584 |
| 4,607,126 | * 8/1986 | Sajtos .................... | 568/385 |
| 4,769,464 | * 9/1988 | Sajtos .................... | 546/314 |
| 5,543,560 | 8/1996 | Pollhammer et al. ........... | 560/234 |

FOREIGN PATENT DOCUMENTS 0614869    9/1994  (EP) ............................ C07C/45/40

* cited by examiner

Primary Examiner—Samuel Barts
Assistant Examiner—Elvis O. Price
(74) Attorney, Agent, or Firm—Ralph J. Mancini

(57) ABSTRACT

The invention pertains to a process for the preparation of glyceraldehyde, or an acetal or a hemiacetal thereof, characterized in that 3-butene-1,2-diol is dissolved in a lower alkanol and is subjected to ozonolysis to obtain a 3-hydroperoxy-3-alkoxy-propane-1,2-diol, which is subjected to a reductive treatment to obtain a hemiacetal of glyceraldehyde, which optionally may be converted into glyceraldehyde or an acetal or hemiacetal thereof, and to a process wherein the hemiacetal of glyceraldehyde is converted to a 3-aminopropane-1,2-diol derivative, by subjecting the hemiacetal of glyceraldehyde to a reductive treatment in the presence of ammonia or a primary or secondary amine. Preferably, the hemiacetal of glyceraldehyde is subjected to a reductive treatment in the presence of an amine with the formula $R_1R_2NH$, wherein $R_1$ and $R_2$ independently are hydrogen or an alkyl group with 1–18 carbon atoms, or $R_1$ and $R_2$ together with the nitrogen atom to which they are bonded form a 5- or 6-membered ring, to give a compound with the formula $R_1R_2N—CH_2—CHOH—CH_2OH$, wherein $R_1$ and $R_2$ have the previously given meanings.

10 Claims, No Drawings

PROCESS FOR THE PREPARATION OF GLYCERALDEHYDE AND DERIVATIVES THEREOF

FIELD OF THE INVENTION

The invention pertains to a process for the preparation of glyceraldehyde, or acetals or hemiacetals thereof, and to 3-aminopropane-1,2-diol derivatives.

BACKGROUND OF THE INVENTION

Processes for preparing glyceraldehyde and acetals or hemiacetals thereof are known. Commonly, glyceraldehyde is made from acrolein or its acetal. In U.S. Pat. No. 2,947,761 a process for preparing glyceraldehyde is disclosed. This process makes use of acrolein as starting material, which is subjected to an epoxidation with hydrogen peroxide followed by ring opening. However, this method suffers from a number of drawbacks. In particular, hydrogen peroxide is a strong oxidizing agent which can transform the carbonyl group of acrolein into a carboxylic acid group, which leads to considerable amounts of side products. A further disadvantage of this method is that great care must be taken to maintain a constant pH level during the epoxidation reaction.

The instant invention has for its object to provide a simple method without the above-mentioned drawbacks.

SUMMARY OF THE INVENTION

The present invention generally relates to a process for the preparation of glyceraldehyde or an acetal or hemiacetal thereof. The process is characterized in that 3-butene-1,2-diol is dissolved in a lower alkanol and subjected to ozonolysis to obtain a 3-hydroperoxy-3-alkoxy-propane-1,2-diol, which is subjected to a reductive treatment to obtain a hemiacetal of glyceraldehyde, which optionally may be converted into glyceraldehyde, or an acetal or a hemiacetal thereof.

DETAILED DESCRIPTION OF THE INVENTION

The invention relates to a process for the preparation of glyceraldehyde or an acetal or hemiacetal thereof wherein 3-butene-1,2-diol is dissolved in a lower alkanol and subjected to ozonolysis to obtain a 3-hydroperoxy-3-alkoxy-propane-1,2-diol, which is subjected to a reductive treatment to obtain a hemiacetal of glyceraldehyde, which optionally may be converted into glyceraldehyde, or an acetal or a hemiacetal thereof. This new method provides glyceraldehyde and derivatives thereof in high yields at low cost, and further has the advantage of avoiding expensive heating procedures during the reaction, using ambient reaction temperatures and low pressures when hydrogen is used as reducing means.

The ozonolysis reaction is performed in such a way that the temperature of the reaction mixture is kept between −25 and +50° C., preferably between −10 and +25° C., and most preferably between 0 and +15° C. In order to prevent the accumulation of hydroperoxides, the ozonolysis is most preferably performed in a continuous manner.

The lower alkanol in which the reaction is performed is an aliphatic or cyclo-aliphatic compound having 1–6 carbon atoms comprising at least one hydroxy group. Lower alkyl alcohols are preferred, in particular methanol and ethanol. Of these, methanol is the most preferred alcohol.

When such lower alkanol is used as the solvent, a hemiacetal of glyceraldehyde can be obtained directly through the lower alkoxyhydroperoxide derivative. The term "alkoxy" refers to the alkoxy group corresponding to the previously mentioned lower alkanol without the hydrogen atom of the hydroxy group. Therefore, it is preferred to make a lower alkoxy hemiacetal of glyceraldehyde, particularly 1-methoxy-propane-1,2,3-triol, but if so desired, the hemiacetal may be converted into the corresponding aldehyde or acetal by methods well known in the art. Acetals can, for example, be prepared by further treatment of the hemiacetal with an excess of an alcohol in an acidic medium. Hemiacetals can easily be hydrolyzed to aldehydes.

The invention further pertains to the synthesis of amine derivatives by converting the hemiacetal of glyceraldehyde into a 3-aminopropane-1,2-diol derivative, by subjecting the hemiacetal of glyceraldehyde to a reductive treatment in the presence of ammonia, or a primary or secondary amine. Preferably, the 3-aminopropane1,2-diol derivative is obtained by subjecting the hemiacetal of glyceraldehyde to a reductive treatment in the presence of an amine with the formula $R_1R_2NH$, wherein $R_1$ and $R_2$ independently are hydrogen or an alkyl group with 1–18 carbon atoms, or $R_1$ and $R_2$ together with the nitrogen atom to which they are bonded form a 5- or 6-membered ring, to give a compound with the formula $R_1R_2N-CH_2-CHOH-CH_2OH$, wherein $R_1$ and $R_2$ have the previously given meanings.

The reductive treatment can be performed in any manner that is known in the art for the reduction of the hydroperoxide intermediate. A convenient method comprises a treatment with hydrogen in the presence of a heterogeneous catalyst. Preferably, the reduction process is performed by continuously feeding the lower alkanol solution of 3-butene-1,3-diol to the reactor in which the reductive treatment is performed, with the hydroperoxide concentration in the reaction mixture being kept as low as possible to avoid side reactions and the accumulation of hydroperoxidic material. Most preferably, the reductive treatment is performed such that the rate of hydroperoxide dosing is low enough to allow the reduction reaction to be completed without an excess of hydroperoxide building up, thereby preventing hydroperoxide accumulation.

If a reductive amination is desired, the reaction can be performed under similar conditions to the reduction procedure, but in the presence of a primary or secondary aliphatic or cyclic amine of the formula $R_1R_2NH$, wherein $R_1$ and $R_2$ independently are hydrogen or an alkyl group with 1–18 carbon atoms, or $R_1$ and $R_2$ together with the nitrogen atom to which they are bonded form a 5- or 6-membered ring. The reductive amination can be performed in a separate reactor after the reductive treatment. Preferably, the reductive treatment and the reductive amination reactions are performed together in one process step in the same reactor in the presence of amine $R_1R_2NH$, using the previously mentioned reduction conditions. The term "alkyl group" also includes branched and unsaturated alkyl groups.

Examples of amines include ammonia, hydrocarbyl primary amines including alkylamine, such as methylamine, ethylamine, propylamine, isopropylamine, butylamine, isobutylamine, isomers of hexylamine, isomers of coco amine, and isomers of (hydrogenated) tallow amine; alkylene diamine, such as ethylene diamine, propylene diamine, isopropylene diamine, butylene diamine, isobutylene diamine, and isomers of hexamethylene diamine; dialkylene triamine, such as diethylene triamine, dipropylene triamine, diisopropyl triamine, isomers of dibutyl triamine, and isomers of dihexyl triamine, trialkylene tetramine, such as triethylene tetramine and isomers of tripropylene tetramine, tetraalkylene pentamine, such as tetraethylene pentamine, pentalkylene hexamine, such as pentaethylene hexamine; dialkyl aminoalkylamine, such as dimethyl aminomethylamine, dimethyl aminoethylamine, dimethyl aminomethylamine, dimethyl aminopropylamine, dimethyl aminobutylamine, dimethyl aminohexylamine, diethyl aminomethylamine, diethyl aminoethylamine, diethyl aminopropylamine, diethyl aminobutylamine, diethyl aminopentylamine, diethyl aminohexylamine, dipropyl aminomethylamine, dipropyl aminoethylamine, dipropyl aminopropylamine, dipropyl aminobutylamine, dipropyl aminopentylamine, dipropyl aminohexylamine, piperidine, azolidine, morpholine, and the like. Aromatic amines can also be used, such as o-, m-, or p-phenylene diamine, alkyl substituted o-, m-, or p-phenylene diamine, aniline, alkylene aniline, including products like methylene dianiline and dimethylene trianiline, polyalkylene aniline, and the like.

Preferably, the reductive alkylation is performed with 1-methoxy-propane-1,2,3-triol and hydrogen on dimethylamine to obtain 3-(dimethylamino)-1,2-propanediol.

The heterogeneous catalyst is selected from a transition metal on active carbon, such as nickel, iron, platinum, palladium, and the like. Palladium on active carbon is a preferred heterogeneous catalyst.

The hydrogenation catalyst may be any catalyst that is known in the art as a hydrogenation catalyst. Preferably, the previously mentioned heterogeneous catalysts are used. Methods of reductive alkylation of glyceraldehyde with amines are known, for instance from U.S. Pat. No. 3,962,338.

An additional advantage of the present process is that the reductive alkylation and the reduction of the 3-hydroperoxy-3-alkoxy-propane-1,2-diol can be combined in one reaction step. Thus the reduction of 3-hydroperoxy-3-alkoxy-propane-1,2-diol with hydrogen and a heterogeneous catalyst is performed in the presence of $R_1R_2NH$, after which the formed hemiacetal of glyceraldehyde is immediately converted into the 3-amino-1,2-propanediol derivative without isolation of an intermediate product.

During the reductive alkylation methylamine, methylalkylamine, methyldialkylamine, and the like are obtained as a side product through reaction with the formaldehyde formed during the ozonolysis. Thus, when dimethylamine is used, 3-(dimethylamino)-1,2-propanediol is obtained and trimethylamine is formed as the side product. The main propanediol derivative can easily be separated from the side product by the usual methods. Thus 3-(dimethylamino)-1,2-propanediol can be separated from trimethylamine by distillation or chromatography.

The invention is illustrated by the following nonlimiting examples.

EXAMPLE 1

Synthesis of 3-(dimethylamino)1,2-propanediol.

In a 1-l flask a 1M solution was prepared of 3-butene-1,2-diol (ex Eastman Chemical Company) and 50 g of decanol (added as an internal standard for GLCP analysis) in methanol. From this vessel, the solution was continuously fed to an ozonolysis reactor. The ozonolysis reactor was comprised of a jacket-cooled glass tube of about 2 cm in diameter and a length of about 10 cm, which was divided up into 5 compartments with sintered glass plates. The 3-butene-1,2-diol solution (at 1.17 ml/min) and ozone (at 1.25 mmoles/min in 1,166 ml of oxygen) were dosed to the bottom of the tube and conducted through the reactor in a co-current operation. The temperature of the jacket cooler was adjusted to obtain a temperature lower than 10° C. for the first compartment. From the top of the reactor, the 3-butene-1,2-diol solution was led to a reservoir, in which a stationary volume of a few milliliters was freed of traces of ozone by nitrogen stripping. The solution was continuously pumped from the reservoir into a 1-l glass autoclave having a gas turbine adjusted to 1,000 rpm and three inlets for the solution, dimethylamine, and hydrogen, respectively. The autoclave contained 20 g of hydrogen-activated 5% palladium type 39 catalyst (ex Johnson Matthey) on active carbon support, 200 ml of methanol, 40 g of dimethylamine, and was adjusted to a constant hydrogen pressure of 2 MPa. The reduction of the formed hydroperoxide and the reductive alkylation of the methoxy hemiacetal of glyceraldehyde were performed at ambient temperature without further cooling until 300 ml of the solution had been converted. The dosing was stopped and the reaction was continued for another 5 min. Thereafter, the mixture was filtered over a sintered metal filter placed in the bottom of the autoclave, to remove the catalyst. The solvent was removed from the filtrate by evaporation, after which 47.82 g of a colourless, slightly viscous oil were obtained. According to gas chromatography analysis, the reaction product was a mixture of 5.86% dimethylformamide, 2% 1,2-butanediol, 62.5% 3-(dimethylamino)-1,2-propanediol corresponding to a yield of 95%, and 27.5% of the internal standard (decanol).

EXAMPLE 2

The procedure of Example 1 was repeated, but starting from a 0.2 M solution of dihydroxybutene together with 10 g of decanol in methanol and using as catalyst 10 g of 10% platinum on activated carbon support (ex Merck) until 80 mmoles of dihydroxybutene were converted. 20 g of dimethylamine were precharged into the autoclave and the reduction or the reductive amination was performed at 40° C. GC analysis of the product material revealed the 3-dimethylamino-1,2-dihydroxypropane yield to be 94%.

EXAMPLE 3

The procedure of Example 1 was repeated, but starting from a 0.2 M solution of dihydroxybutene and 10 g decanol in methanol and using as catalyst 20 g of 5% ruthenium type 97 (ex Johnson Matthey) until 80 mmoles of dihydroxybutene were converted. 12 g of dimethylamine were precharged into the autoclave and the reduction or the reductive amination was performed at 30° C. GC analysis of the product material revealed a yield of 80% 3-dimethylamino-1,2-dihydroxypropane.

EXAMPLE 4

Preparation of glyceraldehyde:

A 1 M methanolic solution of 3-butene-1,2-diol (ex Eastman) was prepared in a volumetric 1-l flask. From this flask, 1.10 ml/min of the solution were continuously fed to the ozonolysis reactor, which was the same as in Example 1. Ozone and the dihydroxybutene solution were dosed to the bottom of the tube and conducted through the reactor in a co-current operation. The temperature of the jacket cooler was adjusted to −1° C., at which the temperature of the first compartment did not rise above 12° C. From the top of the reactor, the readily ozonized solution was led to a reservoir, in which a stationary volume of a few milliliters was freed of ozone traces by nitrogen stripping. From this reservoir, the solution was continuously pumped into the glass autoclave with 20 g of a methanol suspension of 5% palladium type 39 catalyst (ex Johnson Matthey) on active carbon support, and the gas turbine was adjusted to 1,000 rpm. The reactor was adjusted to a constant hydrogen pressure of 2 bar and ambient temperature. After 342 min the dosing was stopped and the reduction was continued for another 20 min. Subsequently, the reaction mixture was removed from the catalyst by filtration over a sintered metal filter placed in the bottom of the autoclave. The solvent was removed from the reaction mixture and 300 ml of water were added to the crude reaction product. In order to remove traces of methanol together with the water, freeze-drying was applied to the reaction mixture. Subsequently, twice times 150 g of water were added and distilled off in order to destroy the hemiacetal and remove the methanol released. Finally, the product was again isolated via freeze-drying after another 300 ml of water had been added. 26.17 g (77%) of glyceraldehyde were isolated as a highly viscous syrup which slowly crystallized.

EXAMPLE 5

Preparation of a long-chain dihydroxypropylamine:

A 1 M methanolic solution of 3-butene-1,2-diol (ex Eastman) was prepared in a volumetric 1-l flask. From this flask, 1.10 ml/min of the solution were continuously fed to the ozonolysis reactor as described in Example 1. Ozone and the 3-butene-1,2-diol solution were dosed to the bottom of the tube and conducted through the reactor in a co-current operation. The temperature of the jacket cooler was adjusted to −1° C., at which the temperature of the first compartment did not rise above 12° C. From the top of the reactor, the readily ozonized solution was led to a reservoir, in which a stationary volume of a few millilitres was freed of ozone traces by nitrogen stripping. From this reservoir, the solution was continuously pumped into the glass autoclave with the gas turbine adjusted to 1,000 rpm. The autoclave contained 20 g of 5% palladium type 39 catalyst (ex Johnson Matthey) on active carbon support, 200 ml of methanol, 134.2 g of Armeen HTD™ (ex Akzo Nobel) and was adjusted to a constant hydrogen pressure of 2 bar and ambient temperature. The dosing was continued for about 260 min. After the dosing was stopped, the reduction was continued for another 50 min. Subsequently, the reaction mixture was removed from the catalyst by filtration over a sintered metal filter in the bottom of the autoclave. After the solvent had been removed in vacuo, 110 g of product were obtained in the form of colourless crystals. In order to determine the distribution of primary, secondary, and tertiary amines, a 0.785 g sample was dissolved in isopropanol and titrated with 0.1M hydrochloric acid with Bromophenol Blue as indicator to give the amount of 27.52 mmoles/g of total amines (primary, secondary, and tertiary). Then, a second sample of 0.786 g was dissolved in isopropanol, after which 5 ml of salicyl aldehyde were added. After stirring for 5 min at 60° C., the sample was treated like the first sample to give a secondary amine value of 24.42 mmole/g. Finally, 5 ml of phenylisothiocyanate were added to 0.880 g of a sample dissolved in isopropanol and stirred at 60° C. for 30 min. Thereafter, the sample was titrated like the previous samples to give a primary amine value of 5.34 mmoles/g.

We claim:

1. A process for the preparation of glyceraldehyde, or an acetal or a hemiacetal thereof, wherein said process comprises dissolving 3-butene-1,2-diol in a lower alkanol in order to form a reaction mixture, subjecting said reaction mixture to ozonolysis in order to obtain a 3-hydroperoxy-3-alkoxy-propane-1,2-diol, which is thereafter subjected to a reductive treatment to obtain a hemiacetal of glyceraldehyde, which is then optionally converted to a glyceraldehyde, or an acetal or a hemiacetal thereof.

2. The process according to claim 1 wherein the lower alkanol is methanol or ethanol.

3. The process according to claim 1 wherein a hemiacetal of glyceraldehyde is prepared.

4. The process of claims 1 wherein the reductive treatment comprises a treatment with hydrogen in the presence of a heterogeneous catalyst.

5. The process according to claim 4 wherein the heterogeneous catalyst comprises a transition metal on active carbon.

6. The process according to claim 5 wherein the heterogeneous catalyst is palladium on active carbon.

7. The process of claim 3 wherein the hemiacetal of glyceraldehyde is subjected to a reductive treatment in the presence of ammonia or a primary or secondary amine in order to obtain a 3-aminopropane-1,2-diol derivative.

8. The process according to claim 7 wherein the hemiacetal of glyceraldehyde is subjected to a reductive treatment in the presence of an amine of the formula:

$$R_1R_2NH$$

wherein $R_1$ and $R_2$ independently selected from the group consisting of hydrogen and an alkyl group with 1–18 carbon atoms, or $R_1$ and $R_2$ together with the nitrogen atom to which they are bonded form a 5- or 6-membered ring, in order to obtain a compound of the formula:

$$R_1R_2N-CH_2-CHOH-CH_2OH$$

wherein $R_1$ and $R_2$ are as defined above.

9. The process according to claim 7 wherein the reductive treatment in the presence of the amine of the formula $R_1R_2NH$ is performed together with the reductive treatment of the 3-hydroperoxy-3-alkoxy-propane-1,2-diol.

10. The process according to claim 8 wherein 3-(dimethylamino)-1,2-propanediol is prepared.

* * * * *